United States Patent  
Lefkowitz et al.

(10) Patent No.: US 6,927,029 B2
(45) Date of Patent: Aug. 9, 2005

(54) SURFACE WITH TETHERED POLYMERIC SPECIES FOR BINDING BIOMOLECULES

(75) Inventors: Steven M. Lefkowitz, Branford, CT (US); Daniel B. Roitman, Menlo Park, CA (US); Nelson R. Holcomb, San Jose, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 42 days.

(21) Appl. No.: 10/005,577

(22) Filed: Dec. 3, 2001

(65) Prior Publication Data

US 2003/0104397 A1 Jun. 5, 2003

(51) Int. Cl.[7] .......................... C12Q 1/68; C12N 11/16; C12M 1/36; C07H 21/04
(52) U.S. Cl. ........................... 435/6; 435/7.1; 435/174; 435/283.1; 435/287.2; 435/287.9; 536/23.1; 536/24.3; 530/300; 530/350
(58) Field of Search .................... 435/6, 7.1, 174, 435/283.1, 287.2, 287.9; 536/23.1, 24.3; 530/300, 350

(56) References Cited

U.S. PATENT DOCUMENTS

| 4,806,546 A | 2/1989 | Carrico et al. |
| 4,806,631 A | 2/1989 | Carrico et al. |
| 4,925,785 A | 5/1990 | Wang et al. |
| 5,053,326 A | 10/1991 | Renz |
| 5,082,935 A | 1/1992 | Cruickshank |
| 5,206,132 A * | 4/1993 | Mitsuhashi ............... 430/567 |
| 5,256,535 A | 10/1993 | Ylikoski et al. |
| 5,514,785 A | 5/1996 | Van Ness et al. |
| 5,550,215 A * | 8/1996 | Holmes ..................... 530/334 |
| 5,622,822 A | 4/1997 | Ekeze et al. |
| 5,624,711 A | 4/1997 | Sundberg et al. |
| 5,643,655 A | 7/1997 | Passarino |
| 5,667,976 A | 9/1997 | Van Ness et al. |
| 5,712,383 A | 1/1998 | Sheridan et al. |
| 5,747,244 A | 5/1998 | Sheridan et al. |
| 5,830,539 A | 11/1998 | Yan et al. |
| 5,919,523 A | 7/1999 | Sundberg et al. |
| 6,281,006 B1 * | 8/2001 | Heller et al. .............. 435/287.9 |
| 6,586,038 B1 * | 7/2003 | Chabrecek et al. ........ 427/2.24 |
| 2002/0001845 A1 * | 1/2002 | Klaerner et al. ............... 436/8 |

FOREIGN PATENT DOCUMENTS

| EP | 0 485 652 A1 | 5/1992 |
| EP | 1 095 711 A2 * | 2/2001 |
| JP | 04-159349 | 1/1994 |
| WO | WO 95/04832 | 2/1995 |
| WO | WO 99/67628 | * 12/1999 |

* cited by examiner

Primary Examiner—BJ Forman
(74) Attorney, Agent, or Firm—Timothy H. Joyce

(57) ABSTRACT

The invention provides a solid support for adsorbing a biomolecule. The support comprises a surface coating having a non-nucleotidic polymer tethered to a surface reactive site. The polymer comprises a backbone, terminus, and adsorbing moieties covalently attached to the backbone and capable of adsorbing a biomolecule that can assume a plurality of conformations. The polymer is generally tethered to the surface at its terminus and the backbone exhibits sufficient mobility and flexibility such that a biomolecule adsorbed by the adsorbing moieties can assume a desired conformation for hybridization. Also provided is a process for preparing a surface coating having a functionalized surface.

20 Claims, 5 Drawing Sheets

SURFACE WITH TETHERED POLYMERIC SPECIES FOR BINDING BIOMOLECULES

TECHNICAL FIELD

The invention relates generally to a surface for adsorption of a biomolecule such as DNA and RNA and more particularly to array fabrication where an adsorbed biomolecule is used as a probe for determining the presence of a particular oligomeric sequence (e.g. polynucleotide sequences) by hybridizing or otherwise binding to complementary oligomers (e.g. polynucleotides).

BACKGROUND

Nucleic acid hybridization is a known method for identifying specific sequences of nucleic acids. Hybridization is based upon pairing between complementary nucleic acid strands. Single-stranded oligonucleotides having known sequences can be used as probes to identify target sequences of nucleic acid analytes, by exposing the probes to sample solutions containing nucleic acid analytes of interest. If a nucleic acid analyte hybridizes to a probe, the analyte necessarily contains the target sequence. Various aspects of this method have been studied in detail. In essence, all variations allow complementary base sequences to pair and to form double stranded molecules. A number of methods are known in the art to determine whether pairing has occurred, such as those described in U.S. Pat. No. 5,622,822 to Ekeze et al. and U.S. Pat. No. 5,256,535 to Ylikoski et al.

Binding DNA to a substrate coating or substrate may involve chemical moieties that are endogenous or exogenous to the DNA. Generally, exogenous moieties are employed in the end attachment approach. For example, the end attachment approach usually involves providing a binding moiety on either the DNA, the substrate coating surface, or both, with the binding moiety attaching the DNA to the surface. For example, DNA containing an exogenous amine at one terminus can be attached to a surface containing an amine reactive moiety (e.g., an aldehyde, epoxide, isothiocyanate, or isocyanate). See, e.g., U.S. Pat. No. 5,215,882 to Bahl et al., and Guo et al., (1994) *Nucleic Acids Research* 22: 5456–65. In such a case, a covalent bond is formed between the amine terminated DNA and the amine reactive moiety of the surface. Body attachment is more commonly used for enzymatically prepared probes that may use chemical functionalities endogenous to DNA (See, e.g., Shalon et al. (1996) *Genome Research* 6,: 639–45) or functionalities that are exogenous to DNA that act as surface binding moieties. Endogenous attachment often involves non-covalent bonding between the surface and the endogenous functionalities. See, e.g., U.S. Pat. No. 5,807,522 to Brown et al. Endogenous attachment techniques have an advantage over exogenous attachment techniques, because there is no need to incorporate additional binding moieties into the DNA, thereby reducing the overall complexity and cost of the process.

When solely endogenous attachment is employed, the surface to which the nucleic acids are to be bound must have reactive sites, e.g., adsorbing or covalent binding moieties, which are capable of covalently or non-covalently binding to endogenous portions of a biomolecule. Examples of such adsorbing or binding moieties can be found in references describing specially modified surfaces for use in solid phase chemistry, including U.S. Pat. Nos. 5,514,785 and 5,667,976 to Van Ness et al., U.S. Pat. Nos. 5,712,383 and 5,747,244 to Sheridan et al., and others. Suitable adsorbing moieties include amide-containing or amine-containing polymers as described in U.S. Pat. Nos. 4,806,631 and 4,806,546 to Carrico et al., PCT Publication No. WO 95/04832, and European Patent Publication No. 458652. Two commonly used attachment surfaces of this type are polylysine-adsorbed glass, and amine-terminated and silated glass.

There are disadvantages, however, to these attachment techniques. It is apparent from the above discussion that exogenous end attachment of polynucleotides requires selective adaption of the polynucleotide termini to bind with the substrate coating surface. Accordingly, the exogenous end attachment technique is not suitable for producing a low cost hybridization assay with a high density of probes bound to a surface. In addition, endogenous body attachment is useful when bound probes are positioned in a manner that allows efficient hybridization to the target. Once the body of a probe nucleotide is endogenously attached to a rigid surface, the mobility of the probe nucleotide is substantially reduced. The significant reduction in mobility compromises the capability of the probe to readily assume a helical conformation and thereby undergo hybridization with the target. Accordingly, endogenous body attachment techniques are inadequate for producing a low-cost hybridization assay with high sensitivity and dynamic range.

Thus, there is a need to provide a method and solid support that allows surface-bound probes sufficient mobility to hybridize efficiently with complementary analytes without exogenous attachment of the probe molecules to the support surface.

SUMMARY OF THE INVENTION

The invention provides a solid support for absorbing a biomolecule, and comprises a surface coating having a surface reactive site, and a non-nucleotide polymer produced on the surface reactive site wherein at least a portion of a biomolecule is capable of being adsorbed by the non-nucleotidic polymer. The invention also provides a process for preparing a solid support capable of adsorbing a biomolecule. The process comprises providing a substrate having a surface reactive site thereon, and contacting the substrate with a polymer or a polymerizable composition under polymerizable conditions to produce a tethered polymer capable of adsorbing at least a portion of a biomolecule.

DETAILED DESCRIPTION OF THE INVENTION

Figure 1:
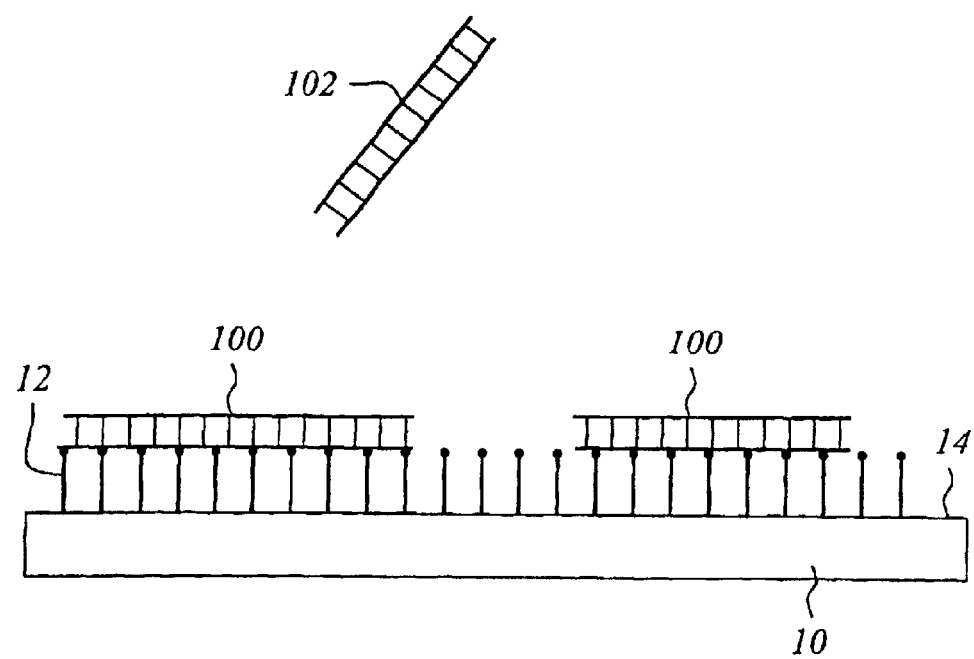
FIG. 1 schematically illustrates how biomolecules such as probe DNA sequences are typically attached to a surface.

Overview and Definitions:

Before describing the present invention in detail, it is to be understood that this invention is not limited to specific compositions, reagents, process steps, or equipment, as such may vary. It is also to be understood that the terminology used herein is for the purpose of describing particular embodiments only, and is not intended to be limiting.

It must be noted that, as used in this specification and appended claims, the singular forms "a", "an" and "the" include plural referents unless the context clearly dictates otherwise. Thus, reference to a polymer comprising "an adsorbing moiety" includes a polymer comprising a plurality of adsorbing moieties. Similarly, a surface coating comprising a surface and "a polymer tethered thereto" includes a surface coating comprising a surface and a plurality of polymers tethered thereto. Also, the term "surface coating" or "surface reactive site" includes a plurality of coatings or reactive sites.

In describing and claiming the present invention, the following terminology will be used in accordance with the definitions set out below.

The term "adsorb" as used herein refers to the noncovalent retention of an external moiety by a solid surface, e.g., by surface-bound moieties. Adsorption of external moieties such as single-stranded DNA by "adsorbing moieties" present on surface-bound tethered polymers may occur through hydrogen bonding, van der Waal's forces, polar attraction of electrostatic forces. Examples of adsorbing moieties include, but are not limited to, amine groups, carboxylic acid moieties, hydroxyl groups, nitroso groups, sulfones and the like. Unless otherwise specified, hybridization is distinct from adsorption.

The term "biomolecule" as used herein refers to an organic molecule that may be found in a living organism or synthetically produced. Typically, biomolecules may include polymers, are large, and may have a complementary counterpart. Examples of biomolecules include, but are not limited to, oligonucleotides, polynucleotides, oligopeptides, peptides, polysacharides and polypeptides.

The term "conformation" as used herein refers to the spatial arrangement of atoms within a molecule. An example of a conformation is the helical conformation of double-stranded DNA.

The term "substrate" or "solid substrate" refers to a rigid or flexible support structure.

The term "substrate coating", "coating" or "surface coating" refers to a non-nucleotide biomolecule, portion of a biomolecule, or chemical moiety attached to or in contact with a substrate and capable of binding nucleotides, polynucleotides, or oligonucleotides. The "surface coating" or "coating" may or may not completely cover the substrate.

The term "functionalization" as used herein relates to modification of a solid substrate to provide a plurality of functional groups on the substrate surface. A "functionalized surface" as used herein refers to a substrate coating that has been modified so that a plurality of functional groups are covalently attached thereto, either directly or indirectly.

The term "monomer" as used herein refers to a chemical entity that can be covalently linked to one or more other such entities to form an oligomer. Examples of monomers include, but are not limited to, addition of polymerizable monomers, typically olefinic monomers such as vinylamine, vinylformamide, acrylic acids, and the like.

The term "polymer" is used herein to indicate a chemical entity that contains a plurality of monomers. As used herein, the term "oligomer" and "polymer" are used interchangeably. Examples of oligomers and polymers include chemical entities that contain repeating units of like, but not necessarily identical chemical structure. In the practice of the instant invention, the tethering monomeric unit of a polymer tethered to a substrate coating may have a different chemical structure from the other monomeric units of the polymer.

The term "polynucleotide" includes both naturally occurring polynucleotides and polynucleotides in which the conventional backbone has been replaced in whole or in part with a non-naturally occurring or synthetic backbone, and those in which one or more of the conventional bases have been replaced with a synthetic base capable of participating in Watson-Crick type hydrogen bonding interactions. Polynucleotides, then, include compounds produced synthetically (For example, PNA as described in U.S. Pat. No. 5,948,902 and reference cited therein) that can hybridize in a sequence specific manner analogous to that of two naturally occurring polynucleotides. Polynucleotides can be single or double stranded. While probes and targets described herein will typically be single-stranded, this is not essential. A "nucleotide" refers to a sub-unit of a polynucleotide and has a phosphate group, a five-carbon sugar and a nitrogen-containing base, as well as analogs of such sub-units. That is, the terms "nucleoside" and "nucleotide" are intended to include those moieties which contain not only the known purine and pyrimidine bases, but also other heterocyclic bases that have been modified. Such modifications include methylated purines and pyrimidines, or other heterocycles. In addition, the terms "nucleoside" and "nucleotide" include those moieties that contain not only the known purine and pyrimidine bases, but also other heterocyclic bases that have been modified. Such modifications include methylated purines and pyrimidines, acylated purines or pyrimidines, or other heterocycles. In addition, the terms "nucleoside" and "nucleotide" include those moieties that contain not only conventional ribose and deoxyribose sugars, but other sugars as well. Modified nucleosides or nucleotides also include modifications on sugar moiety, e.g., wherein one or more of the hydroxyl groups are replaced with halogen atoms of aliphatic groups, or a functionalized as ethers, amines, or the like. The terms "polynucleotide" and "oligonucleotide" are generally used interchangeably, although it is understood in the art that "oligonucleotides" are generally somewhat smaller than "polynucleotides".

The terms "peptide" and "polypeptide" are used to refer to poly (amino acids) wherein the term "amino acid" is intended to include not only the L, D and nonchiral forms of naturally occurring amino acids (alanine, arginine, asparagines, aspartic acid, cysteine, glutamine, glutamic acid, glycine, histidine, isoleucine, leucine, lysine, methionine, phenylalanine, proline, serine, threonine, tryptophan, tyrosine, valine), but also modified amino acids, amino acid analogs, and other chemical compounds which can be incorporated in conventional oligopeptide synthesis, e.g., 4-nitrophenylalanine, isoglutamic acid, isoglutamine, $\epsilon$-nicotinoyl-lysine, isonipecotic acid, tetrahydroisoquinoleic acid, $\alpha$-aminoisobutyric acid, sarcosine, citrulline, cysteic acid, t-butylglycine, t-butylalanine, phenylglycine, cyclohexylalanine, $\beta$-alanine, 4-aminobutyric acid and the like.

The term "probe" is used herein to indicate a molecule having a strong interaction with a specific "target" and capable of hybridizing therewith. Examples of oligomers and polymers suitable for use as a probe include single-stranded polydeoxyribonucleotides (DNA), polyribonucleotides (RNA), other polynucleotides which are/or C-glycosides of a purine or pyrimidine base, polypeptides, and the like.

The term "sample" as used herein relates to a material or mixture of materials, typically, although not necessarily, in fluid form, containing one or more components of interest.

The term "surface reactive site(s)" refers to an initiator attached to a surface that may or may not be activated or initiated for producing a polymer or attaching a pre-synthesized polymer.

The terms "tether" and "tethered" refer to a state of attachment between a polymer and a surface wherein the tethered polymer can extend only a set distance from the point or points at which the polymer is attached to the surface. Tethering is usually accomplished through covalent bonding between a surface and a monomer unit of a polymer. A tethered polymer necessarily has a certain degree of mobility to allow the polymer to assume differing configurations of conformations depending on how the polymer is tethered. A polymer may be tethered to a surface by its terminus, a portion of its body, or combination thereof.

The terms "non-nucleotide" or "non-nucleotide polymer" are used to refer to an amino acid, peptide, oligosaccharide, carbohydrate, polysaccharide, protein fragment or other biological or non-biological material that is not a nucleic acid. The term has broad based meaning to include any polymeric material that may act as a spacer between a surface coating and a biomolecule and which can be extended with repeating or non-repeating units. Non-biological materials include polyvinylethers, polyvinylacrylates, acrylates, ethers and other carbon based materials known in the art.

Accordingly, in one embodiment, the invention provides a modified substrate for adsorbing a biomolecule. The substrate comprises a solid support having a polymer surface coating with reactive surface sites to which a non-nucleotidic polymer is bound. The polymer comprises at least one adsorbing moiety adapted to adsorb an endogenous or exogenous portion of a biomolecule. The polymer is tethered to the surface in a manner such that the polymer is sufficiently mobile and flexible to allow the biomolecule to assume a plurality of conformations following adsorption of the biomolecule to the surface-tethered polymer. The biomolecule, for example, can be an oligomeric probe such as DNA, adapted to hybridize with a sample containing target DNA. Unlike prior coated substrates, the mobility and flexibility of the tethered polymer permits the absorbing moieties to adsorb a biomolecule without significantly decreasing the capability of the adsorbed biomolecule to assume a plurality of conformations.

To highlight the difference between prior techniques and that of the present invention, FIG. 1 schematically illustrates how the body or endogenous portions of biomolecules such as DNA have previously been attached to the surface. First a rigid substrate 10 having a surface 14 is provided, wherein adsorbing moieties 12 are disposed on the substrate 10. These adsorbing moieties may be an integral part of the molecular structure of the material that forms the substrate or may result from a surface modification of the substrate coating, e.g., a coating layer or the like. The adsorbing moieties 12 are capable of adsorbing biomolecules such as single stranded probe DNA 100 that is complementary to target DNA 102. In addition, the adsorbing moieties 12, as may be seen, are immobilized on a substrate coating in a substantially rigid arrangement. The probe DNA that is adsorbed by the adsorbing moieties conforms to the profile of the surface 14. Once adsorbed onto the surface, the probe DNA is also substantially immobilized and has a reduced ability to readily assume a helical conformation to undergo hybridization with the target DNA 102. In other words, the substantially rigid arrangement of the adsorbing moieties interferes with an adsorbed DNA probe to undergo hybridization. Derivatization of a surface coating in this manner is described, for example, in U.S. Pat. No. 5,624,711 to Sundberg et al.

Figure 2A:
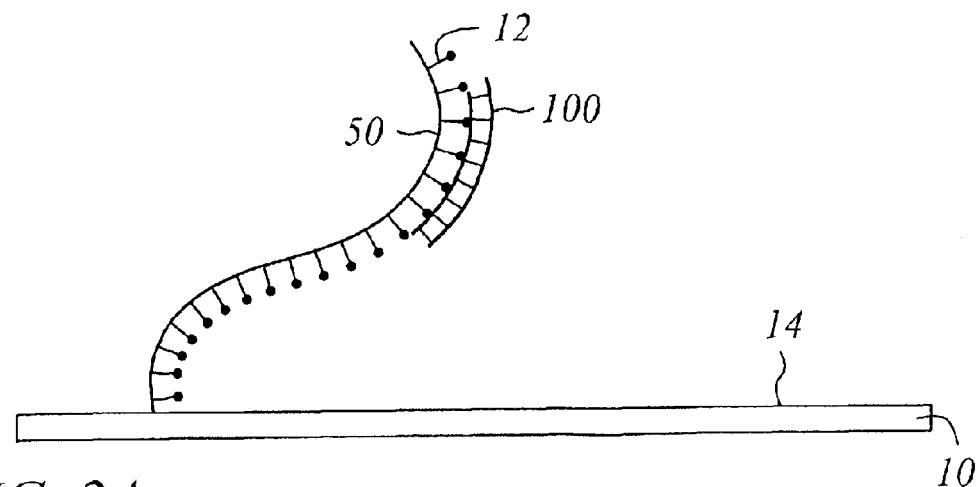
FIG. 2A schematically illustrates an embodiment of the present invention wherein a linear non-nucleotidic polymer having adsorbing moieties thereon is tethered to a surface coating at one terminus of the polymer.
Figure 2B:
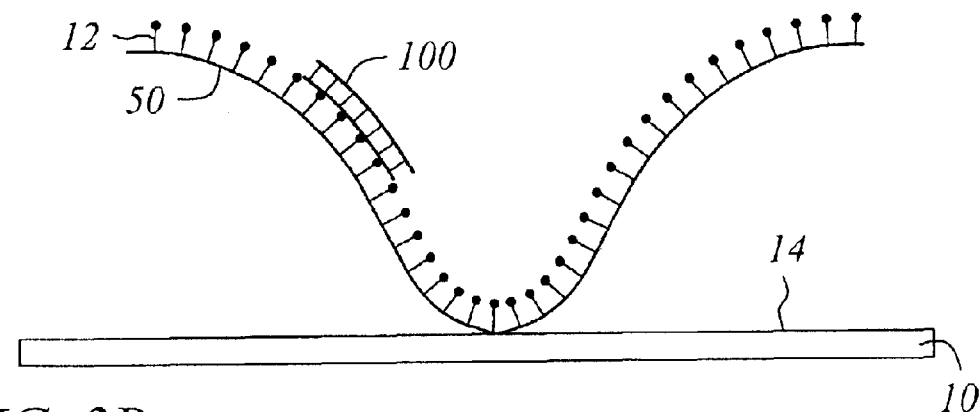
FIG. 2B schematically illustrates an alternative embodiment of the present invention wherein a linear non-nucleotidic polymer having adsorbing moieties thereon is tethered to a surface coating at a point within the backbone of the polymer.
Figure 2C:
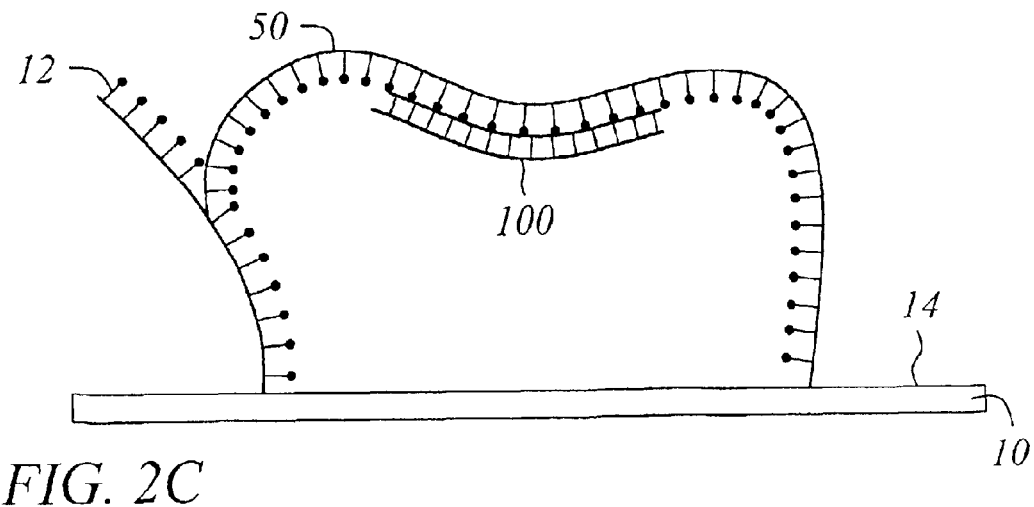
FIG. 2C schematically illustrates an embodiment of the present invention wherein a branched non-nulcleotidic polymer having adsorbing moieties thereon is tethered to a surface coating at both a terminus of the polymer and at a point within the polymer backbone.

FIGS. 2A, 2B, 2C schematically illustrate a modified surface coating of the present invention. Like other articles that adsorb biomolecules, a substrate 10 having a surface 14, is provided. In addition, a non-nucleotidic polymer 50 is also provided that is covalently tethered to surface 14. The polymer comprises adsorbing moieties 12 adapted to adsorb a biomolecule such as probe DNA 100. In each of the FIGS. 2A, 2B, 2C, the polymer is tethered to the surface in a manner such that the polymer 50 is sufficiently mobile and flexible to conform to the probe DNA and allow the adsorbing moiety 12 to adsorb the probe DNA. FIG. 2A shows a linear polymer wherein the polymer is tethered to the surface of the substrate coating at only one point, i.e., the terminus of the polymer. FIG. 2B illustrates a linear polymer wherein the polymer is tethered to the surface of the substrate coating also at only one point, not at a terminus of the polymer, but within the polymer backbone. FIG. 2C illustrates a branched polymer wherein the polymer is tethered to the surface at two points, i.e., at one terminus of the polymer and a point within the polymer backbone. A linear polymer tethered to the surface at one terminus is preferred.

FIGS. 2A, 2B, and 2C show that the adsorbing moieties 12 are pendent to the backbone of the polymer 50. Examples of polymers having pendent adsorbing moieties include, but are not limited to: polyamides and polyamide co-polymers such as poly(acrylamide-co-acrylic acid); polyamines such as poly(vinylamine) and poly(paminostyrene); polypeptides such as poly-L-lysine, cellulosic polymers such as cellulose propionate and nitrocellulose; poly(acrylhydrazide); and vinylic polymers such as poly(acrylic acid), poly(ethylene co-methacrylic acid) and poly(vinylsulfonic acid) and the like. Vinyl polymers such as poly(vinylamine), in which amine groups extend from, but are not necessarily present at the terminus of the poly(vinylamine) structure, are preferred.

It is not necessary that the adsorbing moieties are directly pendent on the backbone of the polymer, i.e., directly bound to an atom contained within the polymer backbone. As shown, the absorbing moieties may be indirectly bound to the backbone, i.e., the adsorbing moiety may extend from one or more monomeric units that are pendent to the backbone. As shown, the adsorbing moieties 12 adsorb the probe DNA in a manner such that the probe DNA is disposed approximately parallel to the backbone of the polymer. In such a case, the body of the DNA is adsorbed on the polymer. However, the probe DNA does not have to be disposed parallel to the backbone of a single strand of the polymer. The probe DNA, for example, may be adsorbed by adsorbing species on more than one strand of tethered polymer as long as the adsorbing moieties that adsorb the probe are not in substantially rigid arrangement. Where a probe DNA is adsorbed, the probe DNA retains sufficient flexibility to assume the necessary helical conformation to allow hybridization of the probe DNA with the target DNA due to the mobility and the flexibility of the polymers and the adsorbing moieties pendent there from.

In addition to polymer flexibility, other factors affecting the adsorption of probe species to the polymers are the polydispersity and the surface-attachment density of the tethered polymers. "Polydispersity" refers to the distribution of the lengths of the polymers that are tethered to the surface. Surface-attachment density refers to the number of polymer chains attached per unit area of the surface. By providing polymers with a variety of lengths and by controlling surface-attachment density, it is possible to optimize the resulting surface to enhance the density of adsorbed probes and thereby increase the yield of hybridization. Typically, although not necessarily, the polymers of the present invention have a molecular weight in the range of at least about 50 to about 2500 Daltons. However, deviations from this range are acceptable as long as sufficient mobility and flexibility of the polymer are retained.

The process for producing the modified substrate coating of the invention can greatly affect the flexibility and mobility of the non-nucleotidic polymer. If a non-nucleotidic polymer having adsorbing moieties is prepared and attached to the coated surface, care must be taken to ensure that the polymer and/or the surface are of structures and/or compositions such that attachment of the polymer results in tethering. In other words, it is important to attach the polymer to the surface coating in a manner such that substantially all of the attached polymer extends away from the surface and retains sufficient mobility and flexibility such that adsorbed biomolecules would be substantially hindered from assuming a desired conformation for hybridization. It is undesirable to attach the polymer in a manner that results in binding of a large portion of the polymer to the surface, since such a case the adsorbing moieties would be bound in a rigid manner. For example, merely applying a solvated polymer to a surface coating, followed by solvent removal, will result in an undesirably rigid or fixed arrangement of surface-bound adsorbing moieties. A probe biomolecule adsorbed by such surface-bound adsorbing moieties will not be able to take on the desired conformation to hybridize with a target molecule. However, if the polymer is attached to a properly functionalized surface that is inert with respect to the polymer except at a specifically selected point. In such a case, the polymer may be sufficiently flexible and mobile to allow an adsorbed probe biomolecule to assume a desired conformation to hybridize with a target biomolecule. This is particularly the case when a polymer is attached to the surface at one terminus thereof. The polymer may also be synthesized on a surface coating rather than attached thereto following polymerization, in which case an initial monomer binds to surface reactive sites present on the surface, and subsequent, successively added monomers bind to the initial monomer to form a polymer.

In either case, the initial surface coating that is used to bind the tethered, nonucleotidic polymer is comprised of a material that has a plurality of surface reactive sites, or is treated or coated so as to have a plurality of reactive sites on its surface. The reactive sites are typically hydrophilic moieties such as hydroxyl groups, carboxyl groups, thiol groups, and/or substituted or unsubstituted amino groups, although, preferably, the reactive hydrophilic moieties are hydroxyl groups. Suitable support materials include, but are not limited to, supports that are typically used for solid phase chemical synthesis, e.g., cross-linked polymeric material (e.g. divinylbenzene styrene-based polymers), agarose (Separose®, cellulosic polymers, polyacrylamides, silica, glass (particularly controlled pore glass, or "CPG"), ceramics, and the like).

In another embodiment, the surface is treated so as to reduce wettability prior to attachment of the nonucleotidic polymer or synthesis thereof on the surface coating. A suitable method for reducing wettability is described in U.S. patent application entitled (Functionalization of Substrate coating Surfaces with Silane Mixtures), and involves functionalization of a substrate coating with a derivatizing composition to produce a low surface energy functionalized surface. The derivatizing composition contains two silanes, a first silane to reduce surface energy and a second silane that provides a reactive site or a functional group that can be converted to a reactive site. The functionalized surface prepared using this process has reactive sites enabling covalent attachment of an intact non-nucleotidic polymer or in situ polymerization using the reactive sites as initiation points, but nevertheless has lowered surface energy so that wettability is reduced and liquid droplets applied to the surface coating are constrained (i.e. do not spread to the extent that they would in the absence of the presently disclosed and claimed surface modification process).

In this embodiment, then, the reactive sites are provided on the substrate coating surface by application of a derivatizing composition containing a first silane that may be represented as $R^1$—Si—$(R^L R^x R^y)$ and a second silane having the formula $R^2$—$(L)_n$—Si—$(R^L R^x R^y)$. In these formulae, the $R^L$, which may be the same or different, are leaving groups, the $R^x$ and $R^y$, which may be the same or different, are either lower alkyl or leaving groups like $R^L$, $R^1$ is a chemically inert moiety that upon binding to the substrate coating surface lowers the surface energy thereof, n is 0 or 1, L is a linking group, and $R^2$ is a reactive site enabling covalent binding of a molecular moiety or a functional group that may be modified to provide such a reactive site. Reaction of the surface coating with the derivatizing composition is carried out under reaction conditions effective to couple the silanes to the surface hydrophilic moieties and thereby provide —Si—$R^1$ groups and —Si—$(l)_n$—$R^2$ groups on the surface coating.

More specifically, the $R^L$ moieties, which are leaving groups, are such that they enable binding of the silanes to the surface. Typically, the leaving groups are hydrolyzable so as to form a silanol linkage to surface hydroxyl groups. Examples of suitable leaving groups include, but are not limited to, halogen atoms, particularly chloro, and alkoxy moieties, particularly lower alkoxy moieties. The $R^x$ and $R^y$ are either lower alkyl, e.g., methyl, ethyl isopropyl, n-propyl, t-butyl, or the like, or leaving groups as just described with respect to $R^L$. Thus, each type silane will generally contain a trichlorosilyl functionality, a tri(lower) alkoxysilyl functionality such as trimethoxysilyl, mixed functionalities such as diisopropylchlorosilyl, dimethylchlorosilyl, ethyldichlorosilyl, methylethylchlorosilyl or the like.

The first silane is the derivatizing agent that reduces surface energy as desired, while the second silane provides the surface functionalization necessary for covalent attachment of an additional molecular moiety, i.e., the non-nucleotidic polymer or a first monomer that serves as the initiation point in an in situ polymerization process. Thus, with respect to the first silane, coupling to the substrate coating yields surface —Si—$R^1$ groups, wherein $R^1$ is a chemically inert moiety that upon binding to the substrate coating surface lowers surface energy. By "chemically inert" is meant that $R^1$ will not be cleaved or modified when the functionalized substrate coating is used for its intended purpose, e.g., in solid phase chemical synthesis, hybridization assays, or the like. Typically, $R^1$ is an alkyl group, generally although not necessarily containing in the range of 2 to 24 carbon atoms, preferably in the range of 10 to 18 carbon atoms. $R^1$ may also be benzyl, either unsubstituted or substituted with 1 to 5, typically 1 to 3, halogen, preferably fluoro atoms. The second silane, upon coupling provides surface —Si—(L)$_n$—R$_2$ groups. Of course, if the R$^X$ and R$^Y$ are not leaving groups, the surface moieties provided will actually be —Si—R$^X$R$^Y$—(L)$_n$—R$^2$. R$^2$ comprises either a reactive site that can bind the non-nucleotidic polymer, or a modifiable group that can be converted to such a reactive site under conditions that do not substantially affect any other chemical species that are present. That is, R$^2$ may be a functional group such as hydroxyl, carboxyl, amino, or the like or it may be a modifiable group such as an olefinic moiety, e.g., a terminal —CH—CH$_2$ group, which can readily be converted to a reactive hydroxyl group by boration and oxidation using procedures known in the art. L represents a linker and n is 0 or 1, such that a linker may or may not be present. If a linker is present, it will generally be a $C_1$–$C_{24}$ hydrocarbylene linking group. Normally, L is $C_1$–$C_{24}$ alkylene, preferably $C_{10}$–$C_{18}$ alkylene.

The density of R$^2$ groups on the surface coating, following reaction with the derivatizing composition, is determined by the relative proportions of the first and second silanes in the derivatizing composition. That is, a higher proportion of the second silanes in the derivatizing composition will provide a greater density of R$^2$ groups, while a higher proportion of the first silane will give rise to a lower density of R$^2$ groups. Optimally, the first silane represents in the range of approximately 0.5 wt % to 50 wt % of the derivatizing composition, preferably in the range of approximately 1.0 wt % to 10 wt % of the composition, while the second silane correspondingly represents in the range of approximately 50 wt % to 99.5 wt % of the derivatizing composition, preferably in the range of approximately 90 wt % to 99 wt % of the composition.

Generally, the non-nucleotidic polymer be synthesized in situ rather than covalently attached after polymerization is complete. During polymerization, it is important that the entire polymer be prevented from being immobilized on the surface coating. This can be accomplished by introducing appropriate monomers or pre-polymers to a solution in contact with the surface having reactive moieties and/or initiation sites. The tethered polymer can be prepared, for example, using the method of Shimomura et al. (1995) *Polymer Journal* 27:974–77, which describes the synthesis of a surface bound poly(acrylic acid), or by other methods known in the art.

Figure 3A:
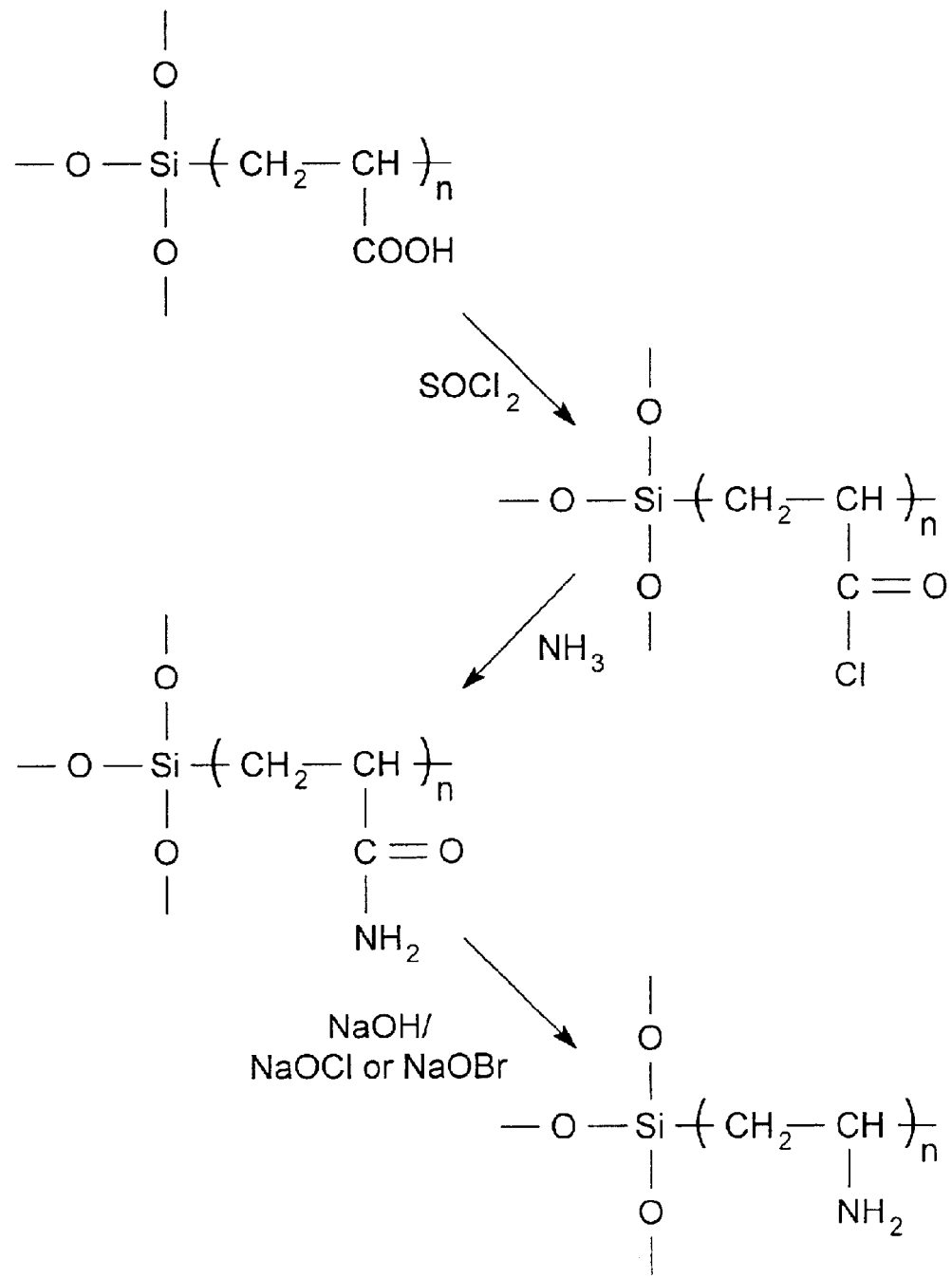
FIG. 3A illustrates the steps of a procedure in which poly(acrylic acid) is converted into poly(vinylamine).
Figure 3B:
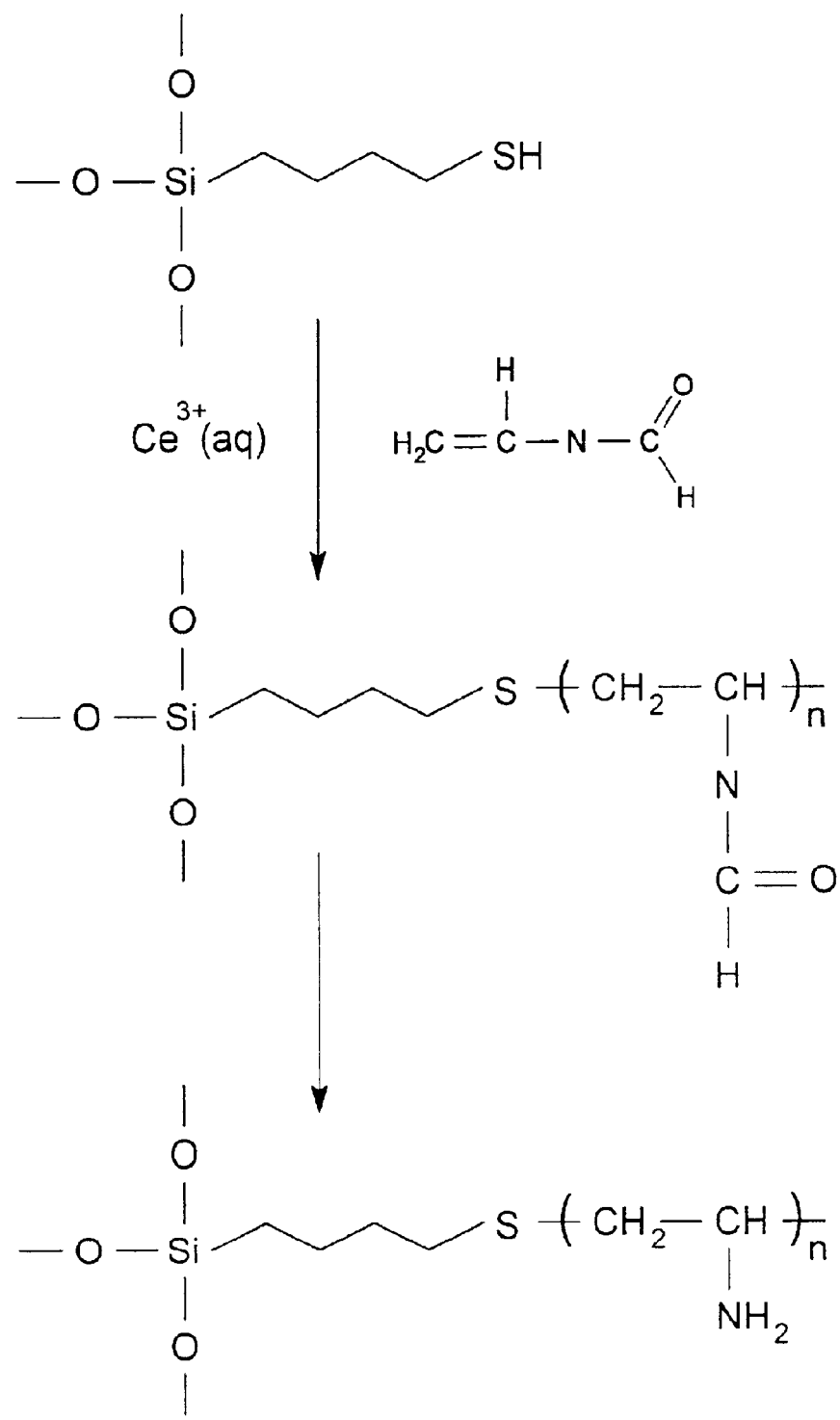
FIG. 3B illustrates the steps of a procedure in which tethered poly(vinylamine) is formed on a functional surface.

FIG. 3A illustrates one example of a process for preparing support-bound tethered polymers, in which, following formation of surface-tethered poly(acrylic acid) via in situ polymerization of acrylic acid monomers, the polymer is converted to poly(acrylamide) by exposure to thionyl chloride to convert the pendent carboxylic acid groups to acryloyl chloride groups (COCl), followed by reaction of ammonia to convert the COCl group into an acrylamide group (CONH$_2$), and contacting the poly(acrylamide) so provided with sodium hypochlorite or sodium hypobromite in the presence of sodium hydroxide, to poly(vinylamine) tethered thereto is illustrated in FIG. 3B. In this process, surface-tethered poly(vinylamine) can be synthesized without first forming a tethered poly(acrylic acid). As illustrated in the figure, poly(vinylamine) can be formed by first initiating polymerization of N-vinylformamide in the presence of aqueous Ce$^{3+}$ ions and a mercatosilane. Monomers other than N-vinylformamide can be added to form copolymers such that spacing of the pendent formamide moieties can be controlled. Once a tethered polymer or copolymer containing monomeric units of N-vinylformamide is formed on the substrate coating surface, the pendent acrylamide groups can be converted to amine moieties by hydrolysis in acid or base.

Once a surface has been prepared in the manner described above, having a tethered nonnucleotidic polymer bound thereto, the surface is contacted with a probe species that is adsorbed by the adsorbing moieties, thereby rendering the probe species substantially immobile with respect to the adsorbing moieties. The surface bound probes can then be used in any chemical or biochemical process involving interaction of the probes with molecular species in a sample to be analyzed, e.g., in hybridization assay to determine the presence of a particular nucleic acid analyte, in chemical separation procedures, in screening processes and the like. In nucleic acid hybridization, the surface bound probes are brought into contact with a sample suspected of containing a particular nucleic acid sequence, the probes and sample are incubated under hybridizing conditions for a time period sufficient to allow hybridization to occur. Hybridization events, if any, are detected using conventional means, e.g., fluorescent or enzymatic label or the like. Such procedures are in current use and will thus be known to those skilled in the art and/or described in the pertinent literature and texts.

Examples

Examples will include at least two types of chemical synthesis processes; generally referred to in the art as "grafting to" and "grafting from" the surface. Generally the process utilizes a polymer with functional moieties capable of forming covalent chemical attachments to the surface, i.e. aldehyde, acid chloride, anhydride, imide, semicarbazide, amine, carboxylic acid, and other functional groups. The surface to be derivatized typically has a stable chemical functional group that may or may not be activated during the coupling process, i.e. hydroxyl, carboxylic acid, olefin, ester, carbonate, amide, and other surface functional groups. The surface functional group may or may not be protected in some manner that both activates and provides more control of the reaction kinetics.

Example 1

Body Attachment Derivatization of Amine Containing Surface Coatings with Reactive Polymer In a clean dry glass reaction vessel 20 g 25% poly(methacryloyl chloride) in dioxane was dissolved in 200 ml anhydrous THF. To the resulting solution was added the substrate coating coated with amine surface functional groups, i.e. amino propyl triethoxy silane coated glass slides. The reaction with the polymer was carried out in a desiccator at room temperature for one hour. Because the acryloyl chloride functional group is not stable under ambient conditions further reaction with a protecting group (NHS, carbonyl imidazole (CI), . . . ) is desirable when the desired probe biomolecule will not be adhered to the surface immediately. Example utilizing NHS: After above reaction the slides are transferred to a fresh solution of 25 g N-hydroxy succinimide in 200 ml dimethyl formamide. The reaction is carried out under anhydrous conditions as above overnight with stirring. Slides are rinsed with absolute ethanol two times and dried under a stream of dry nitrogen gas. Slides are stored in a desiccator until ready for use.

Figure 4A:
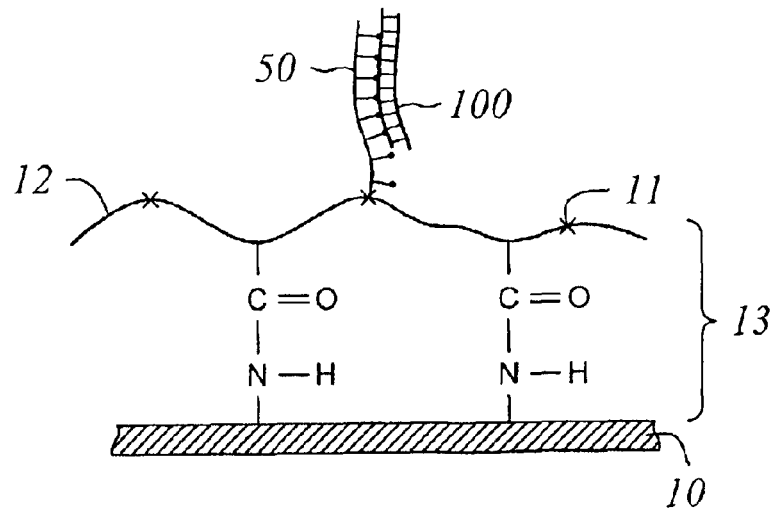
FIG. 4A illustrates another embodiment of the invention.

FIG. 4A shows a schematic representation of another embodiment of the present invention. Substrate 10 may have any number of polymeric films attached to the surface. Surface coating 13 if formed by reaction of an acyl chloride with a silinated amine attached to substrate 10. Although the example shows an amine linkage forming surface coating 13, other bonds and attachments may be used that are well known in the art. Polymer 12 may be attached to substrate 10 with any number of chemistries. The surface coating 13 may orient in a variety of positions and orientations. However, it is important to the invention that there be provided a surface active site X (the surface reactive site is shown as reference numberal 11). In its unreactive form X can be selected from the group consisting of hydroxyl, amino, cyano, and their derivatives as well as halogens such as bromo, chloro, iodo and fluoro. In its reacted form, X is selected from the group consisting of oxygen, nitrogen, carbon, fluorine and boron. The surface active sites X can then be reacted to form the non-nucleotidic polymer 50. Non-nucleotidic polymer 50 can be created through stepwise monomer additions or by pre-synthesizing a defined polymer and then attaching it by reaction with the surface reactive site X. Smith Michael B, March, Jerry, *March's Advanced Organic Chemistry*, 5th Ed., John Wiley and Sons, Inc., 2001, p 506–7; Brownstein, S; Morrison, A; Tan, L. K. *J. Org Chem*, 1985, 50, 2796.

Example 2

Cross-Linking of Surface Adsorbed Polymer Containing Functional Groups, Provides a Covalent Linkage to the Surface for the Adsorbed Polymer In a clean dry reaction vessel was dissolved 7.9 g 3-(triethoxysilyl)propyl succinic anhydride (SAPTES) in 140 ml 1-methyl-2-pyrrolidinone, and 10.7 ml 1M sodium borate buffer at pH 8. Slides coated with adsorbed amine containing polymer (poly acrylamide, poly(3-aminopropylmethyl)siloxane, poly-L-lysine, and the like . . . ) were washed with 50 mM NaOH for 30 seconds and then immediately transferred to the above solution for 30 minutes with stirring at room temperature. Slides were rinsed with DI water for ten minutes and dried by dipping in ethanol for 1 minute followed by a dry nitrogen stream or spin drying. Slides are stored in a desiccator until ready to use to prevent degradation of films.

Figure 4B:
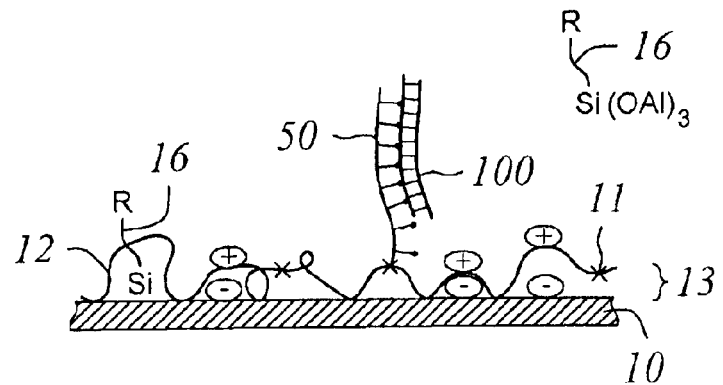
FIG. 4B illustrates a further embodiment of the invention.

FIG. 4B shows a further embodiment of the present invention. A polymer such as polylysine or similarly charged material is attached to substrate 10 through electrostatic, van deer waals, hydrogen bonding etc. FIG. 4B shows a positively charged polylysine polymer attached to a negatively charged silinated surface through electrostatic interaction(s). The polymer forms the surface coating 13 in FIG. 3B. A functionalized linker 16 that contains an R group and a Z group is then reacted with the surface coating 13 to fasten the surface coating 13 to the substrate 10. The functionalized linker 16 is able to attach the surface coating 13 to the substrate 10, because of the spaces between the surface coating 13 and substrate 10. In the functionalized linker, R is selected from the group consisting of amino, hydroxyl, and other nucleophiles well known in the art. Z is selected from the group consisting of thiols, mercaptans, siloxane, silicon, carboxylates, aluminum, alumina, and metals. Functionalized linker 16 is designed so that both electrophiles and nucleophiles may be used on either end of the molecule to fasten the functionalized linker 16 to the substrate 10. Surface coating 13, however, is important, because of the surface active site(s) X (shown as reference numeral 11 in the FIG.) that may be used in attaching or creating the non-nucleotidic polymer 50. Polymer 50 may be grown in situ from site X or may be attached through chemistries well known in the art for deposition. In the case of deposition, the polymer 50 is pre-synthesized and then attached to the surface active site X. After polymer 50 has been constructed through deposition or in situ processes, it may absorb or bind biomolecule 100. Smith Michael B, March, Jerry, *March's Advanced Organic Chemistry*, 5th Ed., John Wiley and Sons, Inc., 2001, p 508–11, 912–4; Farrar, W. V.; *Rec. Chem. Prog.*, 1968, 29, 85; Dayagi, S.; Degani, Y. in Patai *The Chemistry of the Carbon-nitrogen Double Bond*; Ref. 40, p. 64; and Reeves, R. L.; in Patai, Ref2, p. 600.

Example 3

Reaction of Monomer Units with Surface to Provide Oligomeric Base Materials

The initial surface must have a functional group that is either a leaving group or an initiator. This example will utilize a leaving group to initiate a surface reaction, however this would be the same with an initiating group (tertiary benzyl alcohols, hydrazides, peroxides are typical). In a clean dry reactor was added 200 ml dry THF and ~1 g NaH 24 g (60% suspension in toluene), this was stirred to form a suspension. To this was added a 5× excess (25 g) tetraethylene glycol 194 to form an alkoxide substantially on one end of the tetraethylene glycol molecule. To this solution was added bromosilane coated glass slides followed by stirring at room temperature for two hours. Slides were removed and rinsed with copious amounts of water to remove residual base. This was followed by reaction with 200 ml DMF containing 2 mM carbonyldiimidazole 162 to form an ester which reacts with amines, such as triethylenetetramine, the resulting amine can be coupled to the next ethylene glycol layer using the carbonyl imidazole functionalized ethyleneglycol. This procedure can be repeated as many times as desired to form a surface coating that has either hydroxyl or amine surface functional groups depending on when reaction is halted. This example describes a surface coating that is hydrophilic and would provide advantages for depositing biomolecules, the contrasting hydrophobic surface can also be prepared using this technique by simply substituting monomers of choice.

Figure 4C:
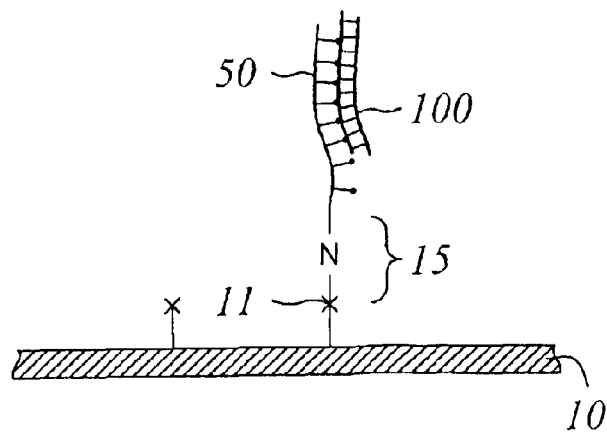
FIG. 4C illustrates another embodiment of the invention.

FIG. 4C shows another embodiment of the present invention. Substrate 10 has a number of functional surface active groups X (shown as reference numeral 11). X is a leaving group that is selected from the group consisting of halogens, isocyantes, alcohols, carbonylamidazoles, maleimnides etc. Functional groups X may react with N to form spacer 15. N and X may be repeating or singular units. N may be selected from the group consisting of alcohols, diols, amines, acid chlorides, semicarbizides, thiols, glycols etc. Non-nucleotidic polymer 50 may be formed in situ from N and/or X or may be pre-synthesized and then deposited and attached by chemistries well known in the art. Non-nucleotidic polymer 50 is then capable of absorbing a biomolecule 100. Smith Michael B, March, Jerry, *March's Advanced Organic Chemistry*, 5th Ed., John Wiley and Sons, Inc., 2001, p 1193; Stachissini, A. S.; do Amaral, L. *J. Org. Chem.* 1991, 56, 1419.

All patents and publications mentioned infra and supra are hereby incorporated by reference.

What is claimed is:

1. A process for preparing a solid support, comprising:
    (a) providing a solid support comprising a surface coating having a surface reactive hydroxyl, carboxyl, amino or thiol group;
    (b) contacting the surface reactive hydroxyl, carboxyl, amino or thiol group with a plurality of monomers;
    (c) polymerizing said monomers to produce a solid support having a surface tethered polymer covalently linked to said surface coating, said surface tethered polymer having at least one adsorbing moiety for adsorbing a biomolecule; and (d) linking a biomolecule to said polymer via said adsorbing moiety.

2. The process of claim 1, wherein a portion of said biomolecule is a linking moiety.

3. The process of claim 1, wherein said polymer is substantially linear.

4. The process of claim 1, wherein said adsorbing moiety is an amine group.

5. The process of claim 1, wherein said biomolecule comprises an oligonucleotide or polynucleotide.

6. The process of claim 1, further comprising polymerizing an additional non-nucleotidic polymer tethered to said surface coating, said non-nucleotidic polymer comprising additional adsorbing moieties for adsorbing additional biomolecules.

7. The method of claim 1, wherein at least one of said monomers reacts with said surface reactive hydroxyl, carboxyl, amino or thiol group to covalently bond said polymer to said surface coating.

8. A process for preparing a solid support capable of adsorbing a biomolecule, comprising:

(a) providing a solid support comprising a surface coating having a surface reactive hydroxyl, carboxyl, amino or thiol group;

(b) contacting the surface reactive hydroxyl, carboxyl, amino or thiol group with a plurality of monomers; and (c) polymerizing said monomers to produce a solid support having a surface tethered polymer covalently linked to said surface coating, said surface tethered polymer having at least one adsorbing moiety for adsorbing a biomolecule, wherein said polymer is a vinyl polymer.

9. The process of claim 8, wherein said vinyl polymer is a poly-(vinylamine).

10. A process for preparing a solid support containing a probe biomolecule capable of hybridization to a target species, comprising:

(a) providing a solid support comprising a surface coating having surface reactive hydroxyl, carboxyl, amino or thiol group, (b) contacting the surface reactive hydroxyl, carboxyl, amino or thiol group with a plurality of monomers; and (c) polymerizing said monomers to produce a solid support having a surface tethered polymer covalently linked to said surface coating, said surface tethered polymer having adsorbing sites for adsorbing biomolecules, wherein said surface tethered polymer is capable of assuming a plurality of conformations and exhibits sufficient mobility and flexibility such that the number of biomolecules adsorbed by the adsorbing moieties is maximized; and (d) contacting the surface tethered polymer with the probe biomolecule.

11. The process of claim 10, wherein a portion of said biomolecule is a linking moiety.

12. The process of claim 11, wherein said vinyl polymer is a poly-(vinylamine).

13. The process of claim 10, wherein said polymer is substantially linear.

14. The process of claim 10, wherein said polymer is a vinyl polymer.

15. The process of claim 10, wherein said adsorbing moieties are amine groups.

16. The process of claim 10, wherein said biomolecule comprises an oligonucleotide or polynucleotide.

17. The process of claim 10, further comprising polymerizing a non-nucleotidic polymer tethered to said surface coating, said non-nucleotidic polymer comprising additional adsorbing moieties adapted to adsorb an additional biomolecule.

18. A process for preparing a solid support capable of adsorbing a biomolecule, comprising:

(a) providing a solid support comprising a surface coating having a surface reactive surface reactive hydroxyl, carboxyl, amino or thiol group;

(b) contacting the surface reactive hydroxyl, carboxyl, amino or thiol group with vinyl monomers; and, (c) polymerizing said monomers to produce a solid support having a surface tethered vinyl polymer covalently linked to said surface coating, said surface tethered vinyl polymer having at least one adsorbing moiety for adsorbing a biomolecule.

19. The process of claim 18, wherein said polymerization is done in the presence of cerium.

20. The process of claim 18, wherein said vinyl polymer is a poly-(vinylamine).

* * * * *